United States Patent [19]

Vandenberk et al.

[11] Patent Number: 5,688,799
[45] Date of Patent: Nov. 18, 1997

[54] 9-HYDROXY-PYRIDO[1,2-A]PYRIMIDIN-4-ONE ETHER DERIVATIVES

[75] Inventors: Jan Vandenberk, Beerse; Ludo Edmond Josephine Kennis, Turnhout, both of Belgium

[73] Assignee: Janssen Pharmaceutica N.V., Beerse, Belgium

[21] Appl. No.: 637,754

[22] PCT Filed: Nov. 16, 1994

[86] PCT No.: PCT/EP94/03804

§ 371 Date: May 3, 1996

§ 102(e) Date: May 3, 1996

[87] PCT Pub. No.: WO95/14691

PCT Pub. Date: Jun. 1, 1995

[30] Foreign Application Priority Data

Nov. 23, 1993 [EP] European Pat. Off. .......... 93203270

[51] Int. Cl.[6] .............. C07D 471/04; C07D 239/00; C07D 221/00; A61K 31/505
[52] U.S. Cl. .............. 514/258; 544/282; 544/283; 544/285; 544/286
[58] Field of Search .............. 544/282, 285, 544/286, 283; 514/258

[56] References Cited

U.S. PATENT DOCUMENTS 5,158,952  10/1992  Janssen et al. .............. 514/258

FOREIGN PATENT DOCUMENTS

| 196132 | 1/1986 | European Pat. Off. ...... C07D 413/14 |
| 368388 | 10/1989 | European Pat. Off. ...... C07D 471/04 |
| 453042 | 4/1991 | European Pat. Off. ...... C07D 471/04 |

OTHER PUBLICATIONS

Chemical Abstracts Service, Registry Notebook Number Section, 1990 Supplement, Registry No. 129678–05–3 through 131249–89–3, p. 4747RS, Compound No. 130049–88–6, 1990.

*Primary Examiner*—John M. Ford
*Assistant Examiner*—Sabiha Qazi
*Attorney, Agent, or Firm*—Charles J. Metz

[57] ABSTRACT

The present invention is concerned with novel compounds having the formula

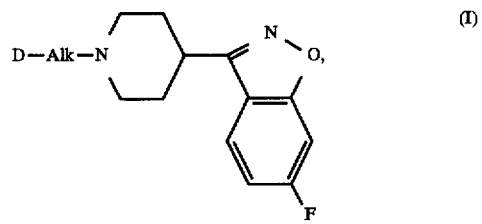

(I)

the pharmaceutically acceptable acid addition salts thereof and the stereochemically isomeric forms thereof, wherein Alk represents $C_{1-4}$alkanediyl;

D is a bicyclic heterocycle of formula

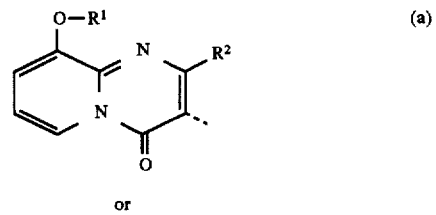

(a)

or

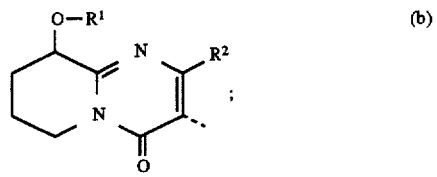

(b)

wherein each $R^1$ independently is $C_{2-6}$alkenyl; $C_{2-6}$alkynyl; $C_{3-6}$cycloalkyl optionally substituted with $C_{1-4}$alkyl; $C_{1-19}$alkyl optionally substituted with $C_{3-6}$cycloalkyl, halo, $C_{1-6}$alkyloxy or cyano; and each $R^2$ independently is hydrogen or $C_{1-4}$alkyl. Novel compounds; compositions; processes for preparing novel compounds and intermediates are described.

22 Claims, No Drawings

9-HYDROXY-PYRIDO[1,2-A]PYRIMIDIN-4-ONE ETHER DERIVATIVES

CROSS-REFERENCE TO RELATED APPLICATIONS

This application is based upon PCT Application Ser. No. PCT/EP 94/03804, filed Nov. 16, 1994, which claims priority from European Patent Application Ser. No. 93.203.270.9, filed on Nov. 23, 1993.

The present invention is concerned with novel compounds having the formula

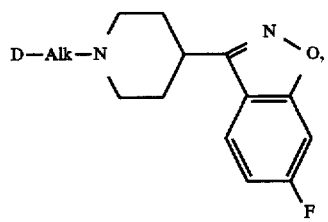

the pharmaceutically acceptable acid addition salts there, of and the stereochemically isomeric forms thereof, useful as neurotransmitter antagonists with increased central activity.

In U.S. Pat. No. 4,804,663 there are described a number of 3-piperidinyl-1,2-benzisoxazoles substituted with, inter alia, a 4H-pyrido[1,2-a]pyrimidin-4-one radical having antipsychotic activity.

In EP-0,368,388-A, published on May 16, 1990, a number of structurally related 3-piperidinyl-1,2-benzisoxazoles substituted with a (6,7,8,9-tetrahydro-4-oxo-4 H-pyrido[1,2-a]pyrimidin-3-yl) radical having a specific hydroxy or $C_{1-19}$alkylcarbonyloxy substitution on the 6,7,8 or 9 position are disclosed.

EP-0,453,042-A, published on Oct. 23, 1991, describes 3-piperidinyl-1,2-benzisoxazoles substituted with 4 H-pyrido-[1,2-a]pyrimidin-4-one having a specific substitution on the 9 position.

The present novel compounds differ from the prior-art by the fact that they invariably have an ether substituent on the 9-position of the pyrido[1,2-a]pyrimidin-4-one moiety or the 6,7,8,9-tetrahydro analogue thereof and unexpectedly show an increased central activity.

The present invention concerns novel compounds having the formula

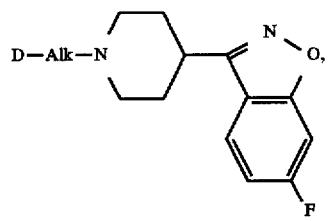

the pharmaceutically acceptable acid addition salts thereof and the stereochemically isomeric forms thereof, wherein Alk represents $C_{1-4}$alkanediyl;

D is a bicyclic heterocycle of formula

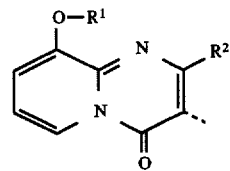

or

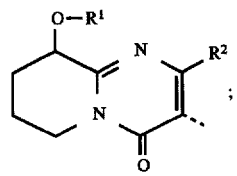

wherein each $R^1$ independently is $C_{2-6}$alkenyl; $C_{2-6}$alkynyl; $C_{3-6}$cycloalkyl optionally substituted with $C_{1-4}$alkyl; $C_{1-19}$alkyl; $C_{1-19}$alkyl substituted with $C_{3-6}$cycloalkyl, halo, $C_{1-6}$alkyloxy or cyano; and each $R^2$ independently is hydrogen or $C_{1-4}$alkyl.

In the foregoing definitions and hereinafter $C_{1-4}$alkanediyl defines bivalent straight and branch chained alkanediyl radicals having from 1 to 4 carbon atoms such as, for example, methylene, 1,2-ethanediyl, 1,3-propanediyl and 1,4-butanediyl; $C_{1-4}$alkyl defines straight and branch chained saturated hydrocarbon radicals having from 1 to 4 carbon atoms such as, for example, methyl, ethyl, propyl, 1-methylethyl, butyl, 1-methylpropyl, 2-methylpropyl and 1,1-dimethyl-ethyl; $C_{1-6}$alkyl defines $C_{1-4}$alkyl radicals as defined hereinabove and the higher homologs thereof having from 5 to 6 carbon atoms such as pentyl and hexyl; $C_{1-6}$alkyl in the term "$C_{1-6}$alkyloxy" is defined as hereinabove; $C_{1-12}$alkyl defines $C_{1-6}$alkyl radicals as defined hereinabove and the higher homologs thereof having 7 to 12 carbon atoms such as, for example, heptyl, octyl, nonyl, decyl, undecyl, dodecyl and the like; $C_{1-19}$alkyl defines $C_{1-12}$alkyl radicals as defined hereinabove and the higher homologs thereof having from 13 to 19. carbon atoms such as, for example, tridecyl, tetradecyl, pentadecyl, hexadecyl, heptadecyl, octadecyl, nonadecyl and the like; halo is generic to fluoro, chloro, bromo and iodo; $C_{3-6}$cycloalkyl defines cyclic hydrocarbon radicals having from 3 to 6 carbon atoms, such as cyclopropyl, cyclobutyl, cyclopentyl or cyclohexyl; $C_{2-4}$alkenyl defines straight and branch chained hydrocarbon radicals containing one double bond and having from 2 to 4 carbon atoms, such as, for example, ethenyl, 2-propenyl, 3-butenyl, 2-butenyl and the like; $C_{2-6}$alkenyl defines $C_{2-4}$alkenyl radicals as defined hereinabove and the higher homologs thereof having 5 to 6 carbon atoms such as, for example, 2-pentenyl, 3-pentenyl, 3-methyl-2-butenyl and the like; $C_{2-4}$alkynyl defines straight and branch chained hydrocarbon radicals containing one triple bond and having from 2 to 4 carbon atoms, such as, for example, ethyn, 2-propynyl, 3-butynyl, 2-butynyl, and the like; $C_{2-6}$alkynyl defines $C_{2-4}$alkynyl radicals as defined hereinabove and the higher homologs thereof having 5 to 6 carbon atoms, such as, for example, 2-pentynyl, 3-pentynyl, 3-hexynyl, and the like.

The term "stereochemically isomeric forms" as used hereinbefore defines all the possible isomeric forms which the compounds of formula (I) may possess. Unless otherwise mentioned or indicated, the chemical designation of compounds denotes the mixture of all possible stereochemically isomeric forms, said mixtures containing all diastereomers and enantiomers of the basic molecular structure.

More in particular, stereogenic centers may have the R- or S-configuration; substituents on bivalent cyclic saturated hydrocarbon radicals may have either the cis- or trans-configuration and alkenyl radicals may have the E- or Z-configuration. Stereochemically isomeric forms of the compounds of formula (I) are obviously intended to be embraced within the scope of this invention.

The compounds of formula (I) have basic properties and, consequently, they may be converted to their pharmaceutically acceptable acid addition salt forms by treatment with appropriate acids, such as, for example, inorganic acids, such as hydrohalic acid, e.g. hydrochloric, hydrobromic acid and the like, sulfuric acid, nitric acid, phosphoric acid and the like; or organic acids, such as, for example, acetic, propanoic, hydroxyacetic, 2-hydroxypropanoic, 2-oxopropanoic, ethanedioic, propanedioic, butanedioic, (Z)-2-butenedioic, (E)-2-butenedioic, 2-hydroxybutanedioic, 2,3-dihydroxybutanedioic, 2-hydroxy-1,2,3-propanetricarboxylic, methanesulfonic, ethanesulfonic, benzenesulfonic, 4-methylbenzenesulfonic, cyclohexanesulfamic, 2-hydroxybenzoic, 4-amino-2-hydroxybenzoic and the like acids. Conversely the salt form can be converted into the free base form by treatment with alkali.

Alk is suitably $C_{1-3}$alkanediyl, especially 1,2-ethanediyl; each $R^1$ independently is suitably $C_{1-12}$alkyl, or $C_{1-4}$alkyl substituted with $C_{1-4}$alkyloxy or cyano; each $R^2$ independently is suitably $C_{1-4}$alkyl, especially methyl.

Interesting compounds are those compounds of formula (I), wherein each $R^1$ is independently $C_{1-19}$alkyl, or $C_{1-19}$alkyl substituted with $C_{1-6}$alkyloxy or cyano.

More interesting compounds are those compounds of formula (I), wherein $R^1$ is $C_{1-12}$alkyl, especially methyl; or $C_{1-4}$alkyl substituted with $C_{1-4}$alkyloxy or cyano, especially ethoxymethyl.

Particular compounds are those compounds of formula (I), wherein each $R^1$ is independently $C_{2-6}$alkenyl or $C_{2-6}$alkynyl.

More particular compounds are those compounds of formula (I), wherein each $R^1$ is independently $C_{2-4}$alkenyl, especially 2-propenyl; or $C_{2-4}$alkynyl, especially 2-propynyl.

An interesting group of compounds are those compounds of formula (I), wherein D is a heterocycle of formula (a).

Another interesting group of compounds are those compounds of formula (I), wherein D is a heterocycle of formula (b).

Preferred compounds are those interesting compounds of formula (I) wherein each $R^2$ is methyl.

Most preferred compounds are:
3-[2-[4-(6-fluoro-1,2-benzisoxazol-3-yl)-1-piperidinyl]ethyl]-6,7,8,9-tetrahydro-9-methoxy-2-methyl-4H-pyrido[1,2a]pyrimidin-4-one;
3-[2-[4-(6-fluoro-1,2-benzisoxazol-3-yl)-1-piperidinyl]ethyl]-6,7,8,9-tetrahydro-2-methyl-9-propoxy-4H-pyrido[1,2-a]pyrimidin-4-one;
3-[2-[4-(6-fluoro-1,2-benzisoxazol-3-yl)-1-piperidinyl]ethyl]-9-methoxy-2-methyl-4H-pyrido[1,2-a]pyrimidin-4-one;
3-[2-[4-(6-fluoro-1,2-benzisoxazol-3yl)-1-piperidinyl]ethyl]-2-methyl-9-(2-propenyloxy)-4H-pyrido[1,2-a]pyrimidin-4-one;
3-[2-[4-(6-fluoro-1,2-benzisoxazol-3-yl)-1-piperidinyl]ethyl]-2-methyl-9-(2-propynyloxy)-4H-pyrido[1,2-a]pyrimidin-4-one;
the pharmaceutically acceptable acid addition salts thereof and the stereochemically isomeric forms thereof.

The compounds of formula (I) can generally be prepared by N-alkylating a 3-piperidinyl-1,2-benzisoxazole of formula (II) with an alkylating reagent of formula (III) following art-known N-alkylation procedures.

D—Alk—W +

(III)

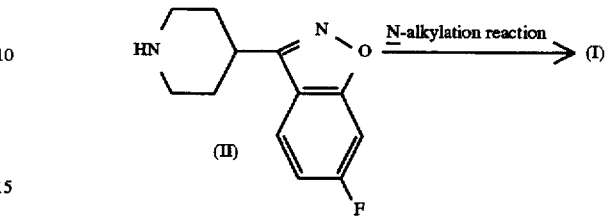

In formula (III) and hereinafter, D is a heterocycle as defined hereinabove, and W represents an appropriate reactive leaving group such as, for example, halo, e.g. chloro, bromo or iodo; sulfonyloxy, e.g. methanesulfonyloxy, 4-methylbenzenesulfonyloxy and the like leaving groups. Said N-alkylation reaction may conveniently be carried out by mixing the reactants, optionally in a reaction-inert solvent such as, for example, water; an aromatic solvent, e.g. benzene, methylbenzene, dimethylbenzene and the like; an alcohol, e.g. ethanol, 1-butanol and the like; a ketone, e.g. 2-propanone, 4-methyl-2-pentanone and the like; an ether, e.g. 1,1'-oxybisethane, tetrahydrofuran, 1,4-dioxane and the like; a dipolar aprotic solvent, e.g. N,N-dimethylformamide, N,N-dimethylacetamide, dimethylsulfoxide, acetonitrile and the like; or a mixture of such solvents. The addition of an appropriate base such as, for example, an alkali metal or an earth alkaline metal carbonate, hydrogen carbonate, hydroxide, oxide, carboxylate, alkoxide, hydride or amide, e.g. sodium carbonate, potassium carbonate, and the like, or an organic base such as, for example, a tertiary amine, e.g. N,N-diethylethanamine, N-(1-methylethyl)-2-propanamine, 4-ethylmorpholine, pyridine and the like, may optionally be used to pick up the acid which is formed during the course of the reaction. Stirring and somewhat elevated temperatures may enhance the rate of the reaction.

In this and the following preparations, the reaction products may be isolated from the medium and, if necessary, further purified according to methodologies generally known in the art such as, for example, extraction, crystallization, trituration and chromatography.

The compounds of formula (I) may also be obtained by the cyclization of an oxime of formula (IV), wherein Y is a reactive leaving group such as, for example, halo or nitro. Preferably Y is a halo group and more particularly fluoro.

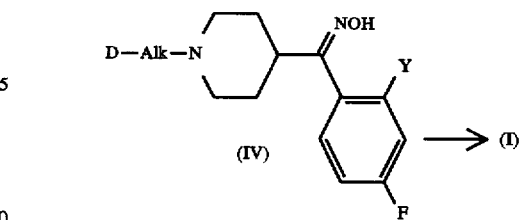

Said cyclization reaction of the oxime of formula (IV) may conveniently be conducted by treatment with an appropriate base, preferably in a suitable reaction-inert solvent at temperatures in the range of 20° to 200° C., preferably at 50° to 150° C., and in particular at the reflux temperature of the reaction mixture. Appropriate bases for said cyclization are, for example, alkali and earth alkaline metal carbonates, hydrogen carbonates, hydroxides, alkoxides or hydrides, e.g. sodium carbonate, sodium hydrogen carbonate, potassium carbonate, sodium hydroxide, sodium methoxide, sodium hydride or organic bases such as amines, e.g. N,N-diethylethanamine, 4-ethylmorpholine and the like bases. Suitable solvents are, for example, water; aromatic hydrocarbons, e.g. methylbenzene, dimethylbenzene and the like; halogenated hydrocarbons, e.g. trichloromethane, 1,2-dichloroethane and the like; alcohols, e.g. ethanol, 1-butanol and the like; ketones, e.g. 2-propanone, 4-methyl-2-pentanone and the like; ethers, e.g. 1,4-dioxane, tetrahydrofuran and the like; dipolar aprotic solvents, e.g. N,N-dimethylformamide, N,N-dimethylacetamide, dimethylsulfoxide and the like, or mixtures of such solvents.

The compounds of formula (I) may also be obtained by art-known Q-alkylation reactions of an intermediate of formula (V-a) or (V-b) with an alkylating reagent of formula $R^1$-W (VI), wherein W is as defined hereinabove, yielding respectively compounds of formula (I-a) or (I-b). Compounds of formula (I-a) are those compounds of formula (I), wherein D is a heterocycle of formula (a). Compounds of formula (I-b) are those compounds of formula (I), wherein D is a heterocycle of formula (b).

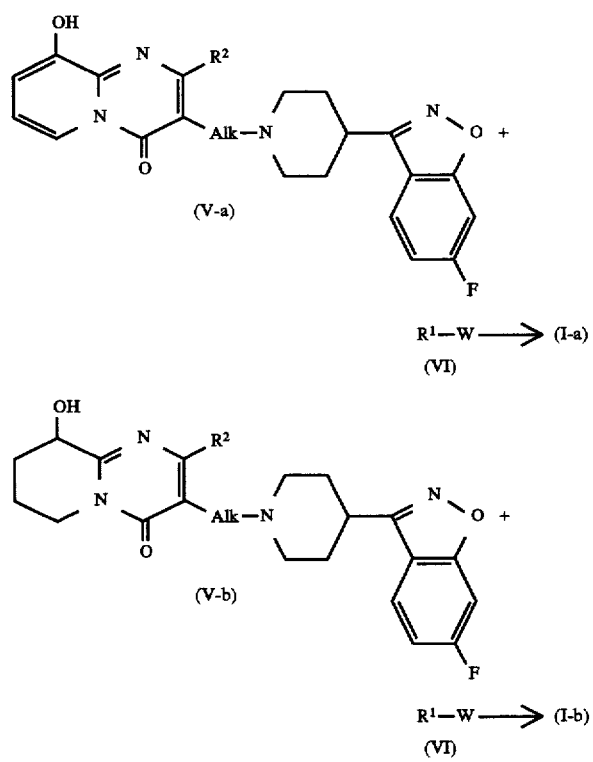

Said Q-alkylation is performed by stirring the reactants in a reaction-inert solvent, such as, for example, water; an aromatic solvent, e.g. benzene, methylbenzene, dimethylbenzene and the like; an alcohol, e.g. ethanol, 1-butanol and the like; a ketone, e.g. 2-propanone, 4-methyl-2-pentanone and the like; an ether, e.g. 1,1'-oxybisethane, tetrahydrofuran, 1,4-dioxane and the like; a dipolar aprotic solvent, e.g. N,N-dimethylformamide, N,N-dimethylacetamide, dimethylsulfoxide, acetonitrile and the like; or a mixture of such solvents. The addition of an appropriate base such as, for example, an alkali metal or an earth alkaline metal carbonate, hydrogen carbonate, hydroxide, oxide, carboxylate, alkoxide, hydride or amide, e.g. sodium carbonate, potassium carbonate, and the like, or an organic base such as, for example, a tertiary amine, e.g. N,N-diethylethanamine, N-(1-methylethyl)-2-propanamine, 4-ethylmorpholine, pyridine and the like, may optionally be used to pick up the acid which is formed during the course of the reaction. Stirring and somewhat elevated temperatures may enhance the rate of the reaction. The intermediates of formula (V-a) are deemed novel.

The compounds of formula (I) may also be converted into each other following art-known transformations. For instance, compounds of formula (I) containing a $C_{2-6}$alkenyl or $C_{2-6}$alkynyl group may be converted into the corresponding compounds containing a $C_{2-6}$alkyl group by art-known hydrogenation techniques.

Intermediates of formula (III), wherein D is a heterocycle of formula (a), said intermediates being represented by formula (III-a), may be prepared by Q-alkylating an intermediate of formula (VII-a) and subsequently transforming the alcohol of formula (VIII-a) into an intermediate of formula (III-a). Said Q-alkylation reaction is performed according to the method described hereinabove for the preparation of compounds of formula (I) starting from intermediates of formula (V).

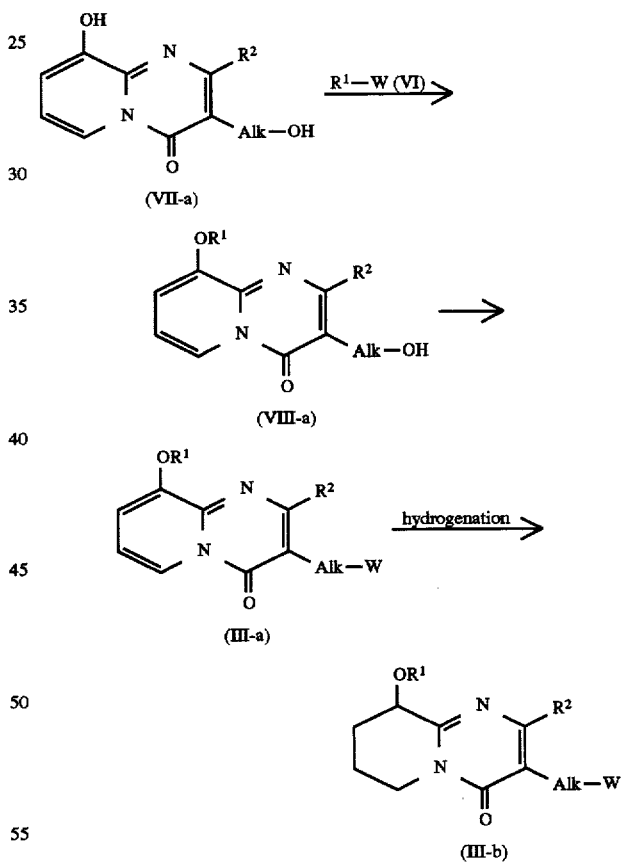

The intermediates of formula (III-a) may be further transformed into intermediates of formula (III-b) by art-known hydrogenation techniques. The reaction steps starting from an intermediate of formula (VIII-a) up to an intermediate of formula (III-b), i.e. transformation of an alcohol group into a reactive leaving group and subsequent hydrogenation, may also be interchanged.

The term acid addition salt as used hereinabove also comprises the solvates which the compounds of formula (I) are able to form and said solvates are meant to be included within the scope of the present invention. Examples of such solvates are e.g. the hydrates, alcoholates and the like.

Some of the compounds of formula (I) and some of the intermediates in the present invention contain at least one asymmetric carbon atom. Pure stereochemically isomeric forms of said compounds and said intermediates can be obtained by the application of art-known procedures. For example, diastereoisomers can be separated by physical methods such as selective crystallization or chromatographic techniques, e.g. counter current distribution, liquid chromatography and the like methods. Enantiomers can be obtained from racemic mixtures by first converting said racemic mixtures with suitable resolving agents such as, for example, chiral acids, to mixtures of diastereomeric salts or compounds; then physically separating said mixtures of diastereomeric salts or compounds by, for example, selective crystallization or chromatographic techniques, e.g. liquid chromatography and the like methods; and finally converting said separated diastereomeric salts or compounds into the corresponding enantiomers.

Pure stereochemically isomeric forms of the compounds of formula (I) may also be obtained from the pure stereochemically isomeric forms of the appropriate intermediates and starting materials, provided that the intervening reactions occur stereospecifically. The pure and mixed stereochemically isomeric forms of the compounds of formula (I) are intended to be embraced within the scope of the present invention.

The compounds of formula (I), as well as intermediates of formula (V), more in particular the intermediates of formula (V-a) or (V-b) the pharmaceutically acceptable acid addition salts and stereochemically isomeric forms thereof, are antagonists of neurotransmitters and in particular of the mediator serotonin. Antagonizing said mediator will suppress or relieve a variety of symptoms associated with phenomena induced by the release, in particular the excessive release, of this mediator. Therapeutic indications for using the present compounds are mainly in the CNS area. However, the present compounds may also show utility in the gastrointestinal and cardiovascular field and related domains. The compounds of formula (I) are particularly useful as antipsychotic agents. Serotonin antagonists are reportedly effective in combatting psychoses, aggressive behaviour, anxiety, depression and migraine. Further the present compounds also appear to be useful therapeutic agents for combatting autism. Further, serotonin is a potent broncho- and vasoconstrictor and thus the present antagonists may be used against hypertension and vascular disorders. In addition, serotonin antagonists have been associated with a number of other properties such as, the suppression of appetite and promotion of weight loss, which may prove effective in combatting obesity; and also the alleviation of withdrawal symptoms in addicts trying to discontinue drinking and smoking habits.

As can be seen from the results in the pharmacological example, the compounds of the present invention penetrate easily into the central nervous system, and consequently have an increased central activity.

The compounds of formula (I) show the additional advantage of being eliminated rather slowly from the body and thus of being long acting. Hence, the compounds of formula (I) only need to be administered at relatively large intervals, e.g. several days or weeks, the actual time of administration depending on the nature of the compound of formula (I) used and the condition of the subject to be treated. Consequently, the present compounds allow for a more efficient therapy: the slow elimination facilitates maintaining a stable plasma concentration at a non-toxic, effective level and the reduction in the number of administrations may be expected to result in better compliance of the subject to be treated with the prescribed medication.

In view of their useful pharmacological properties, the subject compounds may be formulated into various pharmaceutical forms for administration purposes. To prepare the pharmaceutical compositions of this invention, an effective amount of the particular compound, in acid addition salt or base form, as the active ingredient is combined in intimate admixture with a pharmaceutically acceptable carrier, which may take a wide variety of forms depending on the form of preparation desired for administration. These pharmaceutical compositions are desirably in unitary dosage form suitable, preferably, for administration orally, rectally, percutaneously, or by parenteral injection. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions; or solid carriers such as starches, sugars, kaolin, lubricants, binders, disintegrating agents and the like in the case of powders, pills, capsules and tablets. Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable solutions containing compounds of formula (I) may be formulated in an oil for prolonged action. Appropriate oils for this purpose are, for example, peanut oil, sesame oil, cottonseed oil, corn oil, soy bean oil, synthetic glycerol esters of long chain fatty acids and mixtures of these and other oils. Injectable suspensions may also be prepared in which case appropriate liquid carriers, suspending agents and the like may be employed. In the compositions suitable for percutaneous administration, the carrier optionally comprises a penetration enhancing agent and/or a suitable wettable agent, optionally combined with suitable additives of any nature in minor proportions, which additives do not cause any significant deleterious effects on the skin. Said additives may facilitate the administration to the skin and/or may be helpful for preparing the desired compositions. These compositions may be administered in various ways, e.g., as a transdermal patch, as a spot-on or as an ointment. Acid addition salts of (I) due to their increased water solubility over the corresponding base form, are obviously more suitable in the preparation of aqueous compositions.

It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect, in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

In view of the usefulness of the subject compounds in the treatment of diseases associated with the release of neurotransmitters, in particular in the treatment of psychotic diseases, the present invention provides a method of treating warm-blooded animals suffering from such diseases, in particular psychotic diseases, said method comprising the systemic administration of an antipsychotic amount of a compound of formula (I) or a pharmaceutically acceptable acid addition salt thereof, effective in treating diseases associated with the release of neurotransmitters, in particular psychotic diseases. Those of skill in the treatment of such diseases could easily determine the effective mount from the test results presented hereinafter. In general it is contemplated that an effective antipsychotic amount would be from about 0.01 mg/kg to about 4 mg/kg body weight, more preferably from about 0.04 mg/kg to about 2 mg/kg body weight.

The following examples are intended to illustrate and not to limit the scope of the present invention.
Experimental part
A. Preparation of the intermediates

EXAMPLE 1

A mixture of 2-amino-3-pyridinol (0.9 mol), 3-acetyldihydro-2(3H)-furanone (0.8 mol), 4-methylbenzene sulfonic acid (1 g) and dimethylbenzene (700 ml) was stirred and refluxed overnight using a water separator. The mixture was cooled and the product was filtered off and dried. The product was converted into the hydrochloric acid salt in 2-propanol. The salt was filtered off and dried, yielding 120 g (58.4%) of 9-hydroxy-3-(2-hydroxyethyl)-2-methyl-4H-pyrido[1,2-a]pyrimidin-4-one monohydrochloride (interm. 1).

EXAMPLE 2 a) A mixture of 2-amino-3-pyridinol (0.10 mol), sodium hydroxide (50%) (30 ml), 1-chlorododecane (0.20 mol) and methyl-tri-octylammonium chloride (8 g) in benzene (300 ml) was stirred overnight at 80° C. The reaction mixture was cooled. The organic layer was separated, washed with 2N NaOH, dried (MgSO4), filtered and the solvent was evaporated. The residue was cooled and the resulting precipitate was filtered off, washed with hexane, petroleum ether and dried, yielding 21 g (75%) of 3-(dodecyloxy)-2-pyridinamine (interm. 2).

b) A mixture of intermediate (2) (0.050 mol), 3-acetyldihydro-2(3H)-furanone (0.050 mol) and 4-methylbenzene sulfonic acid (1 g) in dimethylbenzene (150 ml) was stirred and refluxed overnight, using a water separator. The solvent was evaporated. The residue was purified over silica gel on a glass filter (eluent: $CH_2Cl_2$/$CH_3OH$ 95/5). The pure fractions were collected and the solvent was evaporated. The residue was crystallized from acetonitrile. The precipitate was filtered off and dried, yielding 13 g (66.9%) of 3-[1-[[3-(dodecyloxy)-2-pyridinyl]amino]ethylidene]dihydro-2(3H)-furanone (interm. 3).

c) Phosphorus oxychloride (75 ml) was added to intermediate (3) (0.025 mol), while stirring. The mixture was stirred and refluxed for 6 hours. The solvent was evaporated. The residue was stirred in ice water and this mixture was alkalized with ammonia. This mixture was extracted with dichloromethane. The separated organic layer was dried, filtered and the solvent was evaporated. The residue was purified over silica gel on a glass filter (eluent: $CH_2Cl_2$/$CH_3OH$ 95/5). The pure fractions were collected and the solvent was evaporated. The residue was crystallized from 2,2'-oxybispropane/acetonitrile. The crystals were filtered off and dried, yielding 8.5 g (83.5%) of 3-(2-chloroethyl)-9-(dodecyloxy)-2-methyl-4H-pyrido[1,2-a]pyrimidin-4-one (interm. 4).

a) Dimethyl sulfate (0.020 mol) was added dropwise to a mixture of intermediate (1) (0.020 mol) and sodium hydroxide (0.020 mol) in water (10 ml), while cooling in ice water. The reaction mixture was stirred for 15 minutes at room temperature, then it was heated for 1 hour using a warm water bath. The reaction mixture was cooled, then extracted with dichloromethane. The separated aqueous layer contained precipitate, which was filtered off and purified by column chromatography over silica gel (eluent: $CH_2Cl_2$/$CH_3OH$ 97/3). The pure fractions were collected and the solvent was evaporated. The residue was crystallized from acetonitrile. The crystals were filtered off and dried, yielding 2 g (42%) of 3-(2-hydroxyethyl)-9-methoxy-2-methyl-4H-pyrido-[1,2-a]pyrimidin-4-one (interm. 5).

b) Methanesulfonyl chloride (0.013 mol) was added dropwise to a stirred and cooled (5° C.) mixture of intermediate (5) (0.0115 mol) and N,N-diethylethanamine (0.013 mol) in dichloromethane (50 ml). The reaction mixture was stirred for 2 hours at room temperature. The reaction mixture was washed with water. The organic layer was separated, dried (MgSO4), filtered and the solvent was evaporated. The residue was crystallized from acetonitrile. The crystals were filtered off and dried, yielding 2.9 g (80%) 9-methoxy-2-methyl-3-[2-[(methylsulfonyl)oxy]ethyl]-4H-pyrido[1,2-a]-pyrimidin-4-one; mp. 180.0° C. (interm. 6).

TABLE 1

![structure with O—R³, N, CH₃, CH₂—CH₂—O—S(=O)(=O)—CH₃]

| Interm. No. | R³ | Physical data |
| --- | --- | --- |
| 6 | $-CH_3$ | mp. 180.0° C. |
| 7 | $-CH_2-O-CH_2-CH_3$ | — |
| 8 | $-CH_2-CH=CH_2$ | — |
| 9 | $-(CH_2)_3-CN$ | — |

EXAMPLE 4 a) A mixture of intermediate (1) (0.050 mol) and potassium carbonate (0.055 mol) in N,N-dimethylformamide (50 ml) was stirred for 1 hour at 60°–70° C. The mixture was cooled to room temperature and 1-methoxy-2-iodoethane (0.055 mol) was added dropwise. The reaction mixture was stirred for 4 hours at 60°–70° C. The solvent was evaporated. The residue was stirred in water and dichloromethane was added. Crystallization resulted. The precipitate was filtered off and recrystallized from acetonitrile. The precipitate was filtered off and dried, yielding 9.2 g (66%) of 3-(2-hydroxyethyl)-9-(2-methoxyethoxy)-2-methyl-4H-pyrido[1, 2-a]pyrimidin-4-one (interm. 10).

b) A mixture of intermediate (10) (0.0179 mol) in phosphorus oxychloride (50 ml) was stirred and refluxed for 2 hours. The solvent was evaporated. The residue was stirred in water and this mixture was alkalized with ammonia. This mixture was extracted with dichloromethane. The separated organic layer was dried, filtered and the solvent was evaporated. The residue was crystallized from 2,2'-oxybispropane/acetonitrile. The precipitate was filtered off and dried, yielding 3 g (57%) of 3-(2-chloroethyl)-9-(2-methoxyethoxy)-2-methyl-4H-pyrido[1,2-a]pyrimidin-4-one (interm. 11).

EXAMPLE 5 a) A mixture of intermediate (5) (0.059 mol) in methanol (250 ml) was hydrogenated at 50° C. with palladium on

11 activated carbon (10%) (2 g) as a catalyst. After uptake of hydrogen (2 eq.), the catalyst was filtered off. The filtrate was evaporated. The residue was purified by column chromatography over silica gel (eluent: CH$_2$Cl$_2$/CH$_3$OH 95/5). The pure fractions were collected and the solvent was evaporated, yielding 10 g (71%) of (±)-6,7,8,9-tetrahydro-3-(2-hydroxyethyl)-9-methoxy-2-methyl-4H-pyrido[1,2-a]-pyrimidin-4-one (interm. 12).

b) Methanesulfonyl chloride (0.030 mol) was added dropwise to a stirred and cooled (ice water bath) mixture of intermediate (12) (0.029 mol) and N,N-diethylethanamine (0.030 mol) in dichloromethane (50 ml). The reaction mixture was stirred for 2 hours at room temperature. The reaction mixture was washed with water. The organic layer was separated, dried (MgSO$_4$), filtered and the solvent was evaporated, yielding 8 g (84%) of (±)-6,7,8,9-tetrahydro-9-methoxy-2-methyl-3-[2-[(methylsulfonyl)oxy]ethyl]-4H-pyrido[1,2-a]pyrimidin-4-one (interm. 13).

In a similar manner there was also prepared:
(±)-9-(ethoxymethoxy)-6,7,8,9-tetrahydro-2-methyl-3-[2-[(methylsulfonyl)oxy]ethyl]-4H-pyrido[1,2-a]pyrimidin-4-one (interm. 14); and
(±)-6,7,8,9-tetrahydro-2-methyl-3-[2-[(methylsulfonyl)oxy]ethyl]-9-propoxy-4H-pyrido[1,2-a]pyrimidin-4-one (interm. 15).

EXAMPLE 6

A mixture of intermediate (4) (0.010 mol) in methanol (250 ml) and hydrochloric acid in 2-propanol (until acid) was hydrogenated with palladium on activated carbon (10%) (2 g) as a catalyst. After uptake of hydrogen (2 eq.), the catalyst was filtered off and the filtrate was evaporated, yielding 4.5 g (100% crude residue) of (±)-3-(2-chloroethyl)-9-(dodecyloxy)-6,7,8,9-tetrahydro-2-methyl-4H-pyrido[1,2-a]pyrimidin-4-one monohydrochloride (interm. 16).

In a similar manner was also prepared:
(±)-3-(2-chloroethyl)-6,7,8,9-tetrahydro-9-(2-methoxyethoxy)-2-methyl-4H-pyrido-[1,2-a]pyrimidin-4-one (interm. 17).

EXAMPLE 7

A mixture of 9-(ethoxymethoxy)-3-[2-[4-(6-fluoro-1,2-benzisoxazol-3-yl)-1-piperidinyl]ethyl]-2-methyl-4H-pyrido[1,2-a]pyrimidin-4-one (0.008 mol) in hydrochloric acid, 12N (25 ml) and ethanol (100 ml) was stirred and refluxed for 6 hours. The reaction mixture was cooled and the precipitate was filtered off and dried, yielding 4 g (95.7%) 3-[2-[4-(6-fluoro-1,2-benzisoxazol-3-yl)-1-piperidinyl]ethyl]-9-hydroxy-2-methyl-4H-pyrido[1,2-a]pyrimidin-4-one.dihydrochloride.sesquihydrate; mp. 288.3° C. (interm. 18).

B. Preparation of the final compounds

EXAMPLE 8

A mixture of intermediate (6) (0.009 mol), 6-fluoro-3-(4-piperidinyl)-1,2-benzisoxazole monohydrochloride (0.009 mol) and sodium carbonate (0.025 mol) in N,N-dimethylformamide (50 ml) was stirred for 6 hours at 80°-90° C. The reaction mixture was cooled to room temperature and the precipitate was filtered off, stirred in water and filtered off again. The solid was crystallized from N,N-dimethylformamide/H$_2$O. The crystals were filtered off and dried, yielding 1.9 g (48%) of 3-[2-[4-(6-fluoro-1,2-benzisoxazol-3-yl)-1-piperidinyl]ethyl]-9-methoxy-2-methyl-4H-pyrido[1,2-a]pyrimidin-4-one; mp. 209.3° C. (comp. 1).

12

TABLE 2

| Co. No. | R$^3$ | Physical data |
|---|---|---|
| 1 | —CH$_3$ | mp. 209.3° C. |
| 2 | —CH$_2$—O—CH$_2$—CH$_3$ | mp. 95.6° C. |
| 3 | —(CH$_2$)$_{11}$—CH$_3$ | mp. 97.1° C. |
| 4 | —CH$_2$—CH=CH$_2$ | mp. 134.0° C. |
| 5 | —(CH$_2$)$_3$—CN | mp. 125.2° C. |
| 6 | —CH$_2$—C≡CH | mp. 175.4° C. |

EXAMPLE 9

A mixture of intermediate (13) (0.012 mol), 6-fluoro-3-(4-piperidinyl)-1,2-benzisoxazole monohydrochloride (0.010 mol) and sodium carbonate (0.025 mol) in N,N-dimethylformamide (50 ml) was stirred for 6 hours at 80°-90° C. The reaction mixture was filtered and the filtrate was evaporated. Water was added to the residue and this mixture was extracted with dichloromethane. The separated organic layer was dried (MgSO$_4$), filtered and the solvent was evaporated. The residue was purified by column chromatography over silica gel (eluent: CH$_2$Cl$_2$/CH$_3$OH 95/5). The pure fractions were collected and the solvent was evaporated. The residue was crystallized from acetonitrile/2,2'-oxybispropane. The crystals were filtered off and dried, yielding 1.6 g (36%) of (±)-3-[2-[4-(6-fluoro-1,2-benzisoxazol-3-yl)-1-piperidinyl]ethyl]-6,7,8,9-tetrahydro-9-methoxy-2-methyl-4H-pyrido[1,2-a]pyrimidin-4-one; mp. 130.8° C. (comp. 7).

TABLE 3

| Co. No. | R$^3$ | Physical data |
|---|---|---|
| 7 | —CH$_3$ | mp. 130.8° C. |
| 8 | —CH$_2$—O—CH$_2$—CH$_3$ | mp. 132.1° C. |
| 9 | —(CH$_2$)$_{11}$—CH$_3$ | — |
| 10 | —(CH$_2$)$_2$—CH$_3$ | mp. 192.8° C./ E-butenedioate |
| 11 | —(CH$_2$)$_2$—O—CH$_3$ | mp. 153.2° C./ E-butenedioate |

C. Pharmacological Example

EXAMPLE 10

The antipsychotic activity of the subject compounds is evidenced by the experimental data obtained in at least one of two different test procedures, viz. the combined apomorphine (APO), tryptamine (TRY) and norepinephrine (NOR) test in rats, and the apomorphine test in dogs. Said combined apomorphine, tryptamine and norepinephrine test is described in Arch. Int. Pharmacodyn., 227, 238–253 (1977) and provides an empirical evaluation of the relative specificity with which drugs may effect particular neurotransmitter systems centrally (CNS) as well as peripherally. In particular, the test demonstrates the antagonistic activity of the tested compounds of formula (I) on dopamine (by preventing the symptoms elicited with the dopamine agonist apomorphine), on serotonin (by preventing the central and peripheral symptoms (convulsions; hyperaemia) elicited with serotonin or tryptamine), and on norepinephrine (by preventing or delaying death upon administration of the $\alpha_2$-agonist norepinephrine). Said apomorphine test in dogs is described in Arzneim.-Forsch. (Drug Res.), 9, 765–767 (1959) and provides a measure of the duration of action of the tested compounds. The tests are carried out following the procedures described in EP-A-0,196,132 and the experimental data are summarized in Table 4.

TABLE 4

| | Combined test in rats, $ED_{50}$ in mg/kg | | | |
|---|---|---|---|---|
| Compound Number | APO | TRY convulsions | TRY hyperaemia | NOR |
| 1 | 0.31 | 0.16 | 0.0025 | 0.08 |
| 2 | 1.25 | 1.25 | 0.01 | 1.25 |
| 3 | >10 | >10 | 1.25 | 10 |
| 4 | 0.31 | 0.31 | 0.005 | 0.16 |
| 5 | 1.25 | 1.25 | 0.005 | 1.25 |
| 6 | <0.63 | <0.63 | NT | <0.63 |
| 7 | 0.02 | 0.02 | 0.00125 | 0.31 |
| 8 | 0.31 | 0.16 | 0.00125 | 0.31 |
| 9 | 10 | 1.25 | 0.01 | 2.5 |
| 10 | 0.08 | 0.08 | 0.002 | 0.16 |
| 11 | 0.31 | 0.63 | 0.00125 | 1.25 |

NT: Not tested

D. Composition examples

"Active ingredient" (A.I.) as used throughout these examples relates to a compound of formula (I), a pharmaceutically acceptable acid addition salt or a stereochemically isomeric form thereof.

EXAMPLE 11

Oral Drops

500 Grams of the A.I. was dissolved in 0.5 l of 2-hydroxypropanoic acid and 1.5 l of the polyethylene glycol at 60°–80° C. After cooling to 30°–40° C. there were added 35 l of polyethylene glycol and the mixture was stirred well. Then there was added a solution of 1750 grams of sodium saccharin in 2.5 l of purified water and while stirring there were added 2.5 l of cocoa flavor and polyethylene glycol q.s. to a volume of 50 l, providing an oral drop solution comprising 10 mg/ml of A.I. The resulting solution was filled into suitable containers.

EXAMPLE 12

Oral Solution

9 Grams of methyl 4-hydroxybenzoate and 1 gram of propyl 4-hydroxybenzoate were dissolved in 4 l of boiling purified water. In 3 l of this solution were dissolved first 10 grams of 2,3-dihydroxybutanedioic acid and thereafter 20 grams of the A.I. The latter solution was combined with the remaining part of the former solution and 12 l 1,2,3-propanetriol and 3 l of sorbitol 70% solution were added thereto. 40 Grams of sodium saccharin were dissolved in 0.5 l of water and 2 ml of raspberry and 2 ml of gooseberry essence were added. The latter solution was combined with the former, water was added q.s. to a volume of 20 l providing an oral solution comprising 5 mg of the active ingredient per teaspoonful (5 ml). The resulting solution was filled in suitable containers.

EXAMPLE 13

Film-Coated Tablets

Preparation of tablet core

A mixture of 100 grams of the A.I., 570 grams lactose and 200 grams starch was mixed well and thereafter humidified with a solution of 5 grams sodium dodecyl sulfate and 10 grams polyvinylpyrrolidone in about 200 ml of water. The wet powder mixture was sieved, dried and sieved again. Then there was added 100 grams microcrystalline cellulose and 15 grams hydrogenated vegetable oil. The whole was mixed well and compressed into tablets, giving 10.000 tablets, each containing 10 mg of the active ingredient.

Coating

To a solution of 10 grams methyl cellulose in 75 ml of denaturated ethanol there was added a solution of 5 grams of ethyl cellulose in 150 ml of dichloromethane. Then there were added 75 ml of dichloromethane and 2.5 ml 1,2,3-propanetriol. 10 Grams of polyethylene glycol was molten and dissolved in 75 ml of dichloromethane. The latter solution was added to the former and then there were added 2.5 grams of magnesium octadecanoate, 5 grams of polyvinylpyrrolidone and 30 ml of concentrated colour suspension and the whole was homogenated. The tablet cores were coated with the thus obtained mixture in a coating apparatus.

EXAMPLE 14

Injectable Solution 1.8 Grams methyl 4-hydroxybenzoate and 0.2 grams propyl 4-hydroxybenzoate were dissolved in about 0.5 l of boiling water for injection. After cooling to about 50° C. there were added while stirring 4 grams lactic acid, 0.05 grams propylene glycol and 4 grams of the A.I. The solution was cooled to room temperature and supplemented with water for injection q.s. ad 1 l, giving a solution comprising 4 mg/ml of A.I. The solution was sterilized by filtration and filled in sterile containers.

We claim:

1. A compound having the formula

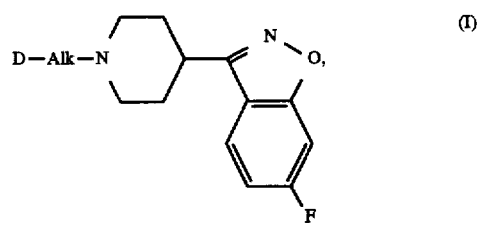

a pharmaceutically acceptable acid addition salt thereof or a stereochemically isomeric form thereof, wherein Alk represents $C_{1-4}$alkanediyl;

D is a bicyclic heterocycle of formula

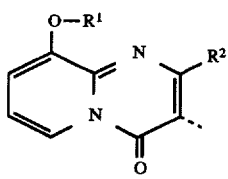

or

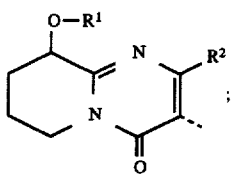

wherein each $R^1$ independently is $C_{2-6}$alkenyl; $C_{2-6}$alkynyl; $C_{3-6}$cycloalkyl optionally substituted with $C_{1-4}$alkyl; $C_{1-10}$alkyl optionally substituted with $C_{3-6}$cycloalkyl, halo, $C_{1-6}$alkyloxy or cyano; and
each $R^2$ independently is hydrogen or $C_{1-4}$alkyl.

2. A compound according to claim 1, wherein $R^2$ is methyl.

3. A compound according to claim 2, wherein Alk is $C_{1-3}$alkanediyl, $R^1$ is $C_{1-12}$alkyl or $C_{1-4}$alkyl substituted with $C_{1-4}$alkyloxy or cyano.

4. A compound according to claim 3, wherein Alk is $C_{1-2}$alkanediyl.

5. A compound according to claim 2, wherein Alk is $C_{1-3}$alkanediyl, $R^1$ is $C_{2-4}$alkenyl or $C_{2-4}$alkynyl.

6. A compound according to claim 5, wherein Alk is $C_{1-2}$alkanediyl.

7. A compound according to claim 1, wherein the compound is
3-[2-[4-(6-fluoro-1,2-benzisoxazol-3-yl)-1-piperidinyl]ethyl]-6,7,8,9-tetrahydro-9-methoxy-2-methyl-4 H-pyrido[1,2-a]pyrimidin-4-one;
3-[2-[4-(6-fluoro-1,2-benzisoxazol-3-yl)-1-piperidinyl]ethyl]-6,7,8,9-tetrahydro-2-methyl-9-propoxy-4 H-pyrido[1,2-a]pyrimidin-4-one;
3-[2-[4-(6-fluoro-1,2-benzisoxazol-3-yl)-1-piperidinyl] ethyl]-9-methoxy-2-methyl-4 H-pyrido[1,2-a]pyrimidin-4-one;
3-[2-[4-(6-fluoro-1,2-benzisoxazol-3-yl)-1-piperidinyl] ethyl]-2-methyl-9-(2-propenyloxy)-4 H-pyrido[1,2-a]pyrimidin-4-one;
3-[2-[4-(6-fluoro-1,2-benzisoxazol-3-yl)-1-piperidinyl] ethyl]-2-methyl-9-(2-propynyloxy)-4H-pyrido[1,2-a] pyrimidin-4-one;
a pharmaceutically acceptable acid addition salt thereof or a stereochemically isomeric form thereof.

8. An intermediate of formula

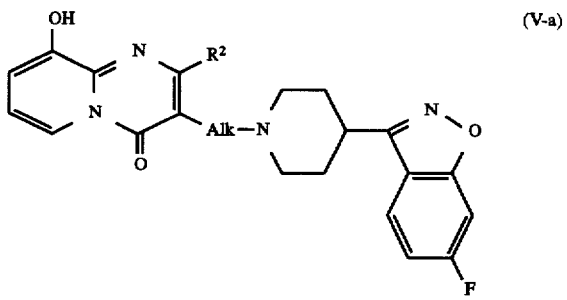

wherein Alk is $C_{1-4}$alkanediyl and $R^2$ is hydrogen or $C_{1-4}$alkyl, a pharmaceutically acceptable acid addition salt thereof or a stereochemically isomeric form thereof.

9. A composition comprising a pharmaceutically acceptable carrier and as active ingredient an effective antipsychotic amount of a compound as claimed in claim 1.

10. A composition comprising a pharmaceutically acceptable carrier and as active ingredient an effective antipsychotic amount of a compound as claimed in claim 2.

11. A composition comprising a pharmaceutically acceptable carrier and as active ingredient an effective antipsychotic amount of a compound as claimed in claim 3.

12. A composition comprising a pharmaceutically acceptable carrier and as active ingredient an effective antipsychotic amount of a compound as claimed in claim 4.

13. A composition comprising a pharmaceutically acceptable carrier and as active ingredient an effective antipsychotic amount of a compound as claimed in claim 5.

14. A composition comprising a pharmaceutically acceptable carrier and as active ingredient an effective antipsychotic amount of a compound as claimed in claim 6.

15. A composition comprising a pharmaceutically acceptable carrier and as active ingredient an effective antipsychotic amount of a compound as claimed in claim 7.

16. A method of treating patients suffering from psychotic diseases which comprises administering to such patients an effective antipsychotic amount of a compound as claimed in claim 1.

17. A method of treating patients suffering from psychotic diseases which comprises administering to such patients an effective antipsychotic amount of a compound as claimed in claim 2.

18. A method of treating patients suffering from psychotic diseases which comprises administering to such patients an effective antipsychotic amount of a compound as claimed in claim 3.

19. A method of treating patients suffering from psychotic diseases which comprises administering to such patients an effective antipsychotic amount of a compound as claimed in claim 4.

20. A method of treating patients suffering from psychotic diseases which comprises administering to such patients an effective antipsychotic amount of a compound as claimed in claim 5.

21. A method of treating patients suffering from psychotic diseases which comprises administering to such patients an effective antipsychotic amount of a compound as claimed in claim 6.

22. A method of treating patients suffering from psychotic diseases which comprises administering to such patients an effective antipsychotic amount of a compound as claimed in claim 7.

* * * * *